United States Patent [19]

Harris et al.

[11] Patent Number: 5,169,974
[45] Date of Patent: Dec. 8, 1992

[54] PROCESS FOR MANUFACTURING ARYLOXYALDEHYDES

[75] Inventors: Gregory D. Harris, Wilmington, Del.; Stanley A. Lee, Macclesfield, United Kingdom

[73] Assignee: Imperial Chemical Industries PLC, London, United Kingdom

[21] Appl. No.: 424,615

[22] Filed: Oct. 20, 1989

[30] Foreign Application Priority Data

Oct. 21, 1988 [GB] United Kingdom ............. 8824672.3

[51] Int. Cl.$^5$ .................. C07C 255/50; C07C 255/52
[52] U.S. Cl. ..................................... 558/414; 568/41; 568/437; 568/488; 568/440; 568/441; 568/483
[58] Field of Search ................ 568/41, 437, 488, 440, 568/441, 483; 558/414

[56] References Cited

U.S. PATENT DOCUMENTS 2,397,412 3/1946 Emerson .............................. 568/437
3,362,997 1/1968 Bolhofer ............................. 568/442
3,419,617 12/1968 Doss ..................................... 568/41

FOREIGN PATENT DOCUMENTS 1295447 11/1972 United Kingdom .

OTHER PUBLICATIONS

Chemical Abstracts, vol. 105, (1986), Abstract No. 225779x.

Primary Examiner—Mary C. Lee
Assistant Examiner—Jacqueline Haley
Attorney, Agent, or Firm—Cushman, Darby & Cushman

[57] ABSTRACT

The invention concerns a novel process for the manufacture of various aryloxyaliphatic aldehydes and related arylthio analogues, which are useful as chemical intermediates. The process involves reacting a dihalogenohydroxyalkane of the formula: $HO.C(R^2)_2.CHX_2$ wherein $R^2$ is alkyl and X is chloro or bromo with a phenol or thiophenol in the presence of base and is applicable to large scale use.

5 Claims, No Drawings

PROCESS FOR MANUFACTURING ARYLOXYALDEHYDES

This invention concerns a novel process and, more particularly, it concerns a novel process for the manufacture of certain aryloxyaliphatic aldehydes and related arylthio analogues, which are useful, for example, as chemical intermediates. Certain of the aldehydes are novel and are provided as a further feature of the invention.

It is known that certain 2-aryloxyalkyl-4-(2-hydroxyphenyl)-1,3-dioxane alkenoic acids are useful as antagonists of one or more of the actions of the prostanoid constrictor substance thromboxane $A_2$ and are of value as pharmaceutical agents (European patent application, no. 201351). The analogous 2-arylthioalkyl derivatives have now also been found to have related pharmacological activity (see our co-pending European patent application). A key intermediate for the production of such alkenoic acids is an aryloxy or arylthio aliphatic aldehyde, which is then reacted either with an erythro-diol derivative or with a 2,2-dialkyl-1,3-dioxane derivative in the presence of an acid catalyst to produce the required 2-(substituted alkyl)-4-(2-hydroxyphenyl)-1,3-dioxane alkenoic acid. Accordingly, there is a need for an efficient synthesis of the appropriate aldehydes usable on a large-scale. It is an object of the invention to provide such a process as an alternative to that which is described in European patent application no. 201351, which latter describes a process involving a diisobutylaluminium hydride reduction at $-70°$ C. of an ester of the appropriate aryloxyalkanoic acid, which process is difficult to perform economically on a large scale because of the need for special plant.

According to the invention there is provided a process for the manufacture of an aliphatic aldehyde derivative of the formula: $R^1.Z.C(R^2)_2.CHO$ [formula I] wherein $R^1$ is an aryl group, Z is oxy or thio, and $R^2$ is a lower alkyl group, which is characterised by reacting a dihalogenohydroxyalkane of the formula: $HO.C(R^2)_2.CHX_2$ [formula II], wherein $R^2$ has the meaning given above and X is chloro or bromo, with a compound of the formula: $R^1.ZH$ [formula III], wherein $R^1$ and Z have the meanings given above, in the presence of base.

It will be appreciated that, under normal conditions, the aldehydes of formula I may exist at least in part in (and be isolated in) the form of hydrate.

Particularly suitable values for $R^1$ include, for example, phenyl and naphthyl, optionally substituted by one or more of a range of substituents, for example, alkyl (especially, lower alkyl such as (1-5C)alkyl, for example, methyl, ethyl or t-butyl), alkoxy (especially, lower alkoxy such as (1-5C)alkoxy, for example methoxy, ethoxy or propoxy), cyano, nitro, trifluoromethyl or halogeno (such as fluoro, chloro and bromo). However, in general the process is suitable for the production of aldehydes with a wide range of aryl or substituted aryl groups as $R^1$, the only limitation being the ability of the phenol or thiophenol of formula III to form a nucleophile in the presence of the base.

Particularly suitable values for $R^2$ include, for example, (1-5C)alkyl and, especially, methyl, ethyl and propyl.

X is preferably chloro.

The process is particularly suitable for the production of compounds of formula I in which $R^1$ is, for example, phenyl, naphthyl and phenyl bearing one or two substituents independently selected from (1-4C)alkyl (such as methyl, ethyl and t-butyl), (1-4C)alkoxy (such as methoxy and ethoxy), halogeno (such as fluoro, chloro and bromo), cyano and nitro, $R^2$ is methyl or ethyl, and Z is, for example, oxy.

A particularly suitable base is, for example, an alkali hydroxide such as lithium, sodium or potassium hydroxide, of which sodium hydroxide is generally preferred on grounds of low cost.

The process is preferably carried out in the presence of a suitable solvent or diluent or a combination thereof, for example in a generally aqueous environment, for example using water or a mixture of water and an ether solvent (such as t-butyl methyl ether, tetrahydrofuran, methoxybenzene or diethyl ether) or a hydrocarbon solvent (such as toluene or xylene). A mixture of a hydrocarbon solvent such as toluene or methoxybenzene with water is a particularly preferred solvent combination for the process.

A phase transfer catalyst such as a tetraalkylammonium halide (for example, cetyltrimethylammonium bromide), may be conveniently used to facilitate the progress of the process. Additionally, the process may be conveniently carried out at a temperature in the general range, for example, $20°–60°$ C., and preferably at or near ambient temperature.

The starting dihalogenohydroxyalkanes of formula II may be obtained by reacting a lower alkyl 2,2-dihalogenoacetate of the formula: $X_2CH.CO.OR^3$ [formula IV] wherein X is chloro or bromo and $R^3$ is lower alkyl (for example, (1-5C)alkyl such as methyl or ethyl), with an excess of a suitable lower alkyl Grignard reagent, for example a lower alkyl magnesium bromide, chloride or iodide, in a suitable solvent or diluent, for example, an ether such as t-butyl methyl ether, diethyl ether, or tetrahydrofuran, at a temperature in the range, for example $-20°$ to $25°$ C.

The process of the invention is particularly advantageous, for example, in avoiding the low temperature, anhydrous reduction step of the prior art process. It is believed that the process may proceed at least in part through the corresponding monohalogeno epoxide of the formula V:

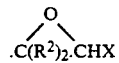

Such an epoxide may be readily obtained in situ, for example, by treating the compound of formula II with base. The invention is to be understood as embracing a modification in which the epoxide of the formula V is used instead of the compound of formula II in the reaction with the compound of the formula $R^1.ZH$.

A number of the aldehydes of formula I are novel, for example, those wherein $R^1$ is phenyl bearing 1 or 2 substituents as defined above, $R^2$ is as defined above, and Z is oxy or thio and are provided as a further feature of the invention.

The conversion of the aldehydes of formula I to the pharmaceutically useful 2-aryloxyalkyl-4-(2-hydroxyphenyl)-1,3-dioxane alkenoic acids is described, for example, in European patent application, publication no. 201351. The aldehydes of formula I are also of use, for example, in the preparation of the corresponding carboxylic acids and alcohols by conventional oxidation and reduction processes, respectively, well known in the art.

The invention will now be illustrated by the following non-limiting Examples in which, unless otherwise stated:

(i) concentrations and evaporations were carried out by rotary evaporation at about 60° C. in vacuo at about 2650 Pa pressure;

(ii) operations were carried out at room temperature, that is in the range 18°–26° C.;

(iii) flash column chromatography was performed on Fluka Kieselgel 60 (catalogue no. 60738) obtained from Fluka A.G., Buchs, Switzerland CH-9470;

(iv) yields are given for illustration only and are not necessarily the maximum attainable by diligent process development; and (v) proton NMR spectra were normally determined at 90 or 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet et cetera.

EXAMPLE 1

Cetyltrimethyl ammonium bromide (0.28 g, 0.77 mmol) was added to a solution of 3-bromophenol (6.66 g, 38.5 mmol) in 3.85M aqueous sodium hydroxide solution (10 ml), followed by a solution of 1,1-dichloro-2-hydroxy-2-methylpropane (A) (1.37 g, 9.6 mmol) in ether (20 ml). The mixture was stirred under an argon atmosphere for 18 hours then diluted with ether (50 ml), and extracted with 2M aqueous sodium hydroxide solution (4×30 ml), to remove unreacted phenol. The combined aqueous extracts were extracted with ether (50 ml), and the organic phase was washed with 2M aqueous sodium hydroxide solution (20 ml) followed by water (50 ml). The combined organic extracts were dried ($MgSO_4$), concentrated, and purified by flash column chromatography, eluting with ethyl acetate/hexane (1:10 v/v), to give 2-(3-bromophenoxy)-2-methylpropanal (0.89 g), as an oil; NMR: 1.45(6H,s), 6.75–7.20(4H,m), 9.8(1H,s).

The starting 2-hydroxy-2-methylpropane derivative (A) was obtained as follows:

A solution of methyl dichloroacetate (77.18 g, 0.54 mol) in anhydrous ether (50 ml) was added to a stirred solution of methyl magnesium iodide [prepared from magnesium turnings (32.8 g, 1.35 mol) and methyl iodide (84.1 ml, 1.35 mol)] in anhydrous ether (750 ml) at 0° C. under an argon atmosphere, at such a rate that the temperature did not rise above 15° C. The mixture was stirred at 25° C. for 30 minutes then cooled to 0° C. Water (100 ml) was added and the mixture was acidified to pH4 with concentrated hydrochloric acid. The layers were separated and the aqueous phase extracted with ether (3×100 ml). The combined organic extracts were dried ($MgSO_4$) and concentrated. The residual oil was distilled under reduced pressure to give 1,1-dichloro-2-hydroxy-2-methylpropane (A) (57.81 g), as an oil; 48°–50° C. at 20 mmHg; NMR: 1.45 (6H,s), 2.15 (1H,br s) and 5.65 (1H,s).

The 1,1-dichloro-2-hydroxy-2-methylpropane A may also be obtained in similar yield by reaction with methyl magnesium bromide or chloride instead of methyl magnesium iodide.

EXAMPLES 2–8

Using an analogous procedure to that described in Example 1 for the preparation of 2-(3-bromophenoxy)-2-methylpropanal, but starting from the appropriate phenol, the following aldehydes were obtained as distillable oils:

(Example 2): 2-methyl-2-phenoxypropanal; NMR: 1.4 (6H,s), 6.8–7.4(5H,m) and 9.8(1H,s);

(Example 3): 2-(4-bromophenoxy)-2-methylpropanal; NMR: 1.4(6H,s), 6.7–7.4(4H,m), 9.8(1H,s);

(Example 4): 2-(4-fluorophenoxy)-2-methylpropanal; NMR: 1.4(6H,s), 6.8–7.0(4H,m), 9.8(1H,s).

(Example 5): 2-(3-fluorophenoxy)-2-methylpropanal; NMR: 1.45(6H,s), 6.55–7.3(4H,m), 9.8(1H,s);

(Example 6): 2-(4-cyanophenoxy)-2-methylpropanal; NMR: 1.5(6H,s), 6.85–7.6(4H,m), 9.75(1H,s);

(Example 7): 2-(4-methoxyphenoxy)-2-methylpropanal; NMR: 1.36(6H,s), 3.76(3H,s), 6.7–6.9(4H,m), 9.85(1H,s); and (Example 8): 2-(4-t-butylphenoxy)-2-methylpropanal; NMR: 1.26(9H,s), 1.41(6H,s), 6.7–7.3(4H,m), 9.85(1H,s).

EXAMPLES 9–10

Using an analogous procedure to that described in Example 1 for the preparation of 2-(3-bromophenoxy)-2-methylpropanal, but starting from the appropriate phenol, the following aldehydes were obtained as distillable oils:

(Example 9): 2-methyl-2-(2-methoxyphenoxy)propanal; NMR: 1.35(6H, s), 3.75(3H, s) and 6.80–7.25(4H, m); and (Example 10): 2-methyl-2-(2-methylphenoxy)propanal; NMR: 1.45(6H, s), 2.25(3H, s) and 6.60–7.20(4H, m).

EXAMPLES 11–12

Using an analogous procedure to that described in Example 1 for the preparation of 2-(3-bromophenoxy)-2-methylpropanal, but starting from the appropriate thiophenol, the following aldehydes were obtained as distillable oils:

(Example 11): 2-methyl-2-(phenylthio)propanal; NMR: 1.25(6H,s), 7.25(5H,m), 9.28(1H,s); m/e 194(M+$NH_4$)+; and (Example 12): 2-methyl-2-(4-fluorophenylthio)propanal; NMR: 1.31(6H,s), 6.99(2H,m), 7.36(2H,m), 9.28(1H,s); m/e 216(M+$NH_4$)+.

EXAMPLE 13

A solution of methyl dichloroacetate (35.7 g, 0.25 mol) in toluene (200 ml) was added dropwise to a stirred solution of methylmagnesium chloride in tetrahydrofuran (250 ml of a 3.0M solution) with cooling to keep the temperature below 20° C. The mixture was stirred at ambient temperature for 3 hours and then treated at less than 5° C. with a mixture of water (200 ml) and concentrated hydrochloric acid (66 ml) to adjust the pH to 2–3. Vigorous stirring and external cooling was need to keep the temperature below 30° C. The two phases which formed were separated and the aqueous phase was extracted with toluene (50 ml). The combined organic phase was washed acid free with brine (200 ml) and water (150 ml).

The toluene solution of 1,1-dichloro-2-hydroxy-2-methylpropane obtained above was added to a solution of sodium hydroxide (100 g) and phenol (240 g) in water (340 ml) with vigorous stirring and stirring continued for 16 to 24 hours. The phases were then separated. The organic phase was washed thoroughly with 4–6M sodium hydroxide solution (3×150 ml) to remove excess phenol and then with water (2×150 ml) until the washings were of low alkalinity. The solvent was removed by rotary evaporation and the residual oil distilled to give 2-methyl-2-phenoxypropanal as a clear oil (b.p. 96°±8° C. at about 2650 Pa pressure) in 61% yield.

EXAMPLE 14

The procedure described in Example 13 was repeated using an equivalent quantity of methyl magnesium bromide (1.5M solution in tetrahydrofuran) instead of methyl magnesium chloride to give 2-methyl-2-phenoxypropanal in 40-65% yield.

What is claimed is:

1. A process for the manufacture of an aliphatic aldehyde of the formula:

$$R^1.Z.C(R^2)_2.CHO$$

wherein $R^1$ is selected from phenyl and naphthyl, unsubstituted or substituted by one or more substituents selected from lower alkyl, lower alkoxy, cyano, nitro, trifluoromethyl and halogeno, Z is oxy or thio, $R^2$ is lower alkyl group, that is characterized by reacting a dihalogenohydroxyalkane of the formula:

$$HO.C(R^2)_2.CHX_2$$

or the corresponding epoxide of the formula

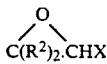

wherein $R^2$ has the meaning given above and X is chloro or bromo, with a compound of the formula:

$$R^1.ZH$$

wherein $R^1$ and Z have the meanings given above, in the presence of an alkali metal hydroxide.

2. A process according to claim 1 characterised in that $R^1$ is phenyl, naphthyl, or phenyl bearing one or two substituents independently selected from methyl, ethyl, t-butyl, methoxy, ethoxy, fluoro, chloro, bromo, cyano and nitro, $R^2$ is methyl or ethyl, and Z is oxy.

3. A process according to claim 1 characterised in that the reaction is carried out in the presence of water and at a temperature in the range of 20°–60° C.

4. A process according to claim 3 characterised in that the reaction is carried out in a mixture of a hydrocarbon solvent selected from the group consisting of toluene, xylene and methoxybenzene, and water.

5. The process according to claim 1 wherein said process is performed in the liquid phase.

* * * * *